United States Patent
Gan et al.

(10) Patent No.: US 11,103,445 B2
(45) Date of Patent: *Aug. 31, 2021

(54) COSMETIC COMPOSITIONS

(71) Applicant: Mary Kay Inc., Addison, TX (US)

(72) Inventors: David Gan, Southlake, TX (US);
Geetha Kalahasti, Addison, TX (US);
Lisha VanPelt, Addison, TX (US)

(73) Assignee: Mary Kay Inc., Addison, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/546,059

(22) Filed: Aug. 20, 2019

(65) Prior Publication Data
US 2020/0138699 A1 May 7, 2020

Related U.S. Application Data

(63) Continuation of application No. 14/958,252, filed on Dec. 3, 2015, now Pat. No. 10,426,723.

(60) Provisional application No. 62/086,790, filed on Dec. 3, 2014, provisional application No. 62/103,942, filed on Jan. 15, 2015.

(51) Int. Cl.
A61K 36/00 (2006.01)
A61K 8/99 (2017.01)
A61K 8/34 (2006.01)
A61Q 19/00 (2006.01)
A61K 8/9706 (2017.01)
A61K 8/9789 (2017.01)

(52) U.S. Cl.
CPC ............ *A61K 8/99* (2013.01); *A61K 8/34* (2013.01); *A61K 8/9706* (2017.08); *A61K 8/9789* (2017.08); *A61Q 19/00* (2013.01); *A61K 2800/28* (2013.01); *A61K 2800/70* (2013.01); *A61K 2800/85* (2013.01)

(58) Field of Classification Search
None
See application file for complete search history.

(56) References Cited

U.S. PATENT DOCUMENTS

| | | |
|---|---|---|
| 5,091,171 A | 2/1992 | Yu et al. |
| 5,422,370 A | 6/1995 | Yu et al. |
| 5,444,091 A | 8/1995 | Rapaport et al. |
| 5,547,988 A | 8/1996 | Yu et al. |
| 5,554,597 A | 9/1996 | Yu et al. |
| 5,554,652 A | 9/1996 | Yu et al. |
| 5,561,158 A | 10/1996 | Yu et al. |
| 6,159,480 A | 12/2000 | Tseng et al. |
| 6,162,774 A | 12/2000 | Charlton et al. |
| 6,328,987 B1 | 12/2001 | Marini |
| 6,709,663 B2 | 3/2004 | Espinoza |
| 6,743,434 B1 | 6/2004 | Lundmark et al. |
| 8,034,385 B2 | 10/2011 | Golz-Berner et al. |
| 8,193,155 B2 | 6/2012 | Maes et al. |
| 8,226,956 B2 | 7/2012 | Bishop et al. |
| 8,715,700 B2 | 5/2014 | Chang et al. |
| 2003/0190300 A1 | 10/2003 | Scancarella et al. |
| 2008/0119527 A1 | 5/2008 | Baldo |
| 2012/0121737 A1 | 5/2012 | Vielhaber et al. |
| 2012/0189651 A1 | 7/2012 | John |
| 2013/0309217 A1 | 11/2013 | Schmidt |
| 2014/0017341 A1 | 1/2014 | Gourlaouen |
| 2016/0008245 A1 | 1/2016 | Durkee et al. |
| 2020/0138699 A1 | 5/2020 | Gan et al. |

FOREIGN PATENT DOCUMENTS

| | | | |
|---|---|---|---|
| CA | 2065664 | 10/1992 | |
| CN | 102177253 | 9/2011 | |
| CN | 102448450 | 5/2012 | |
| CN | 103237555 | 8/2013 | |
| CN | 105250164 A | 1/2016 | |
| CN | 105663018 A | 6/2016 | |
| FR | 2832631 | 5/2003 | |
| FR | 2985183 | 7/2013 | |
| JP | 2001508424 | 6/2001 | |
| KR | 1020030023398 | 3/2003 | |
| KR | 1020100061881 | 6/2010 | |
| WO | WO 94/27569 | 12/1994 | |
| WO | WO 2004/019961 | 3/2004 | |
| WO | WO 2009/087242 | 7/2009 | |
| WO | WO-2009087242 A2 * | 7/2009 | ........... A23C 9/1307 |
| WO | WO 2010/025341 | 3/2010 | |
| WO | WO 2012/154903 | 11/2012 | |

(Continued)

OTHER PUBLICATIONS

"A Natural Active to Strengthen and Soothe Sensitive Skin", Retrieved from the internet URL:https://www.cosmeticsandtoiletries.com/formulating/function/active/231619821.html dated Nov. 12, 2013.
"Barnet Comeotherapy", Retrieved from the internet URL:https://www.barnet.products.com/ dated Jan. 24, 2016.
"Cranberry Pumpkin Salt Scrub", Internet Citation, URL:http://www.naturalbeautyworkshop.com/my_weblog/2008/11/cranberry-pumpk.html retrieved on Sep. 29, 2009.
"Exo-T: The Exotic Skin Regenerator", Retrieved from the internet URL:http://www.lucasmeyercosmetics.com/en/products/product.php?id=20 Retrieved on Oct. 15, 2018.
"How To: Choose the Right Scrub for Your Skin", Retrieved from the Internet: URL:https://www.birchbox.com/guide/article/how-to-choose-the-right-scrub-for-your-skin retrieved Feb. 19, 2016.
"PMD Neuro Neutralizing Toner", Retrieved from the internet, URL:https://getpmd.com/product/pmd-neuro-neutralizing-toner/ retrieved on Feb. 22, 2016.

(Continued)

Primary Examiner — Russell G Fiebig
(74) Attorney, Agent, or Firm — Norton Rose Fulbright US LLP

(57) ABSTRACT

Disclosed is a method of exfoliating skin. The method can include topically applying an effective amount of a composition to skin in need thereof. The composition can include an alpha hydroxy acid, 4-tert-butylcyclohexanol, an aqueous extract of plankton comprising an exopolysacchride synthesized by *Vibo alginolyticus*, an aqueous extract of *Phragmites communis*, an aqueous extract of *Poria cocos*, and an aqueous extract of *Cucurbita pepo* (pumpkin) seed.

14 Claims, No Drawings

(56) References Cited

FOREIGN PATENT DOCUMENTS

| | | |
|---|---|---|
| WO | WO 2013/149323 | 10/2013 |
| WO | WO 2013/182998 | 12/2013 |

OTHER PUBLICATIONS

"Pumpkin seed oil & Sea Salt Body Scrub", Internet citation, URL:http://web.archive.org/web/20071223173208/http://naturesbathandbeauty.com/pumpkin-seed-oil-sea-salt-scrub/ Retrieved on Sep. 29, 2009.

"Rehab London Scrub Up Daily Detox1Birchbox", Retrieved from the internet: Url:https://www.birchbox.com/shop/rehab-london-scrub-up-daily-detox/ retrieved Feb. 19, 2016.

"Soliance-Ocaline: Preventative care for sensitive skin and immediate soother", Retrieved from the internet URL: www.skiloconesplus.com/wp/wp-content/uploads/2017/1_O/Ocaline.pdf retrieved in 2017.

"The Skin Care Benefits of Alpha Hydroxy Acids", Retrieved from the internet URL:https://www.everydayhealth.com/skin-and-beauty/alpha-hydroxy-acids.aspx Retrieved on Oct. 15, 2018.

Database GNPD, Mintel, "Very Gentle Cleansing Cream", Database accession No. 2118292, Feb. 2014.

Dr. Diana Howard, "Methods of Exfoliation", Retrieved from the internet URL:http//www.dermalinstitute.com/us/library/20_article_Methods_of_Exfoliation_html dated Jul. 3, 2013.

Drouillard et al., "Structure of the Exopolysaccharide Secreted by a Marine Strain Vibrio alginolyticus" *Marine Drugs* 2018, 16, 12 pages.

International Cosmetic Ingredient Dictionary and Handbook, 12th edition, vol. 1, p. 331 (2008).

International Cosmetic Ingredient Dictionary and Handbook, 12th edition, vol. 1, p. 60 (2008).

International Search Report and Written Opinion issued in PCT/US2015/063746, dated Jul. 1, 2016.

Tung et al., "a-Hydroxy Acid-Based Cosmetic Procedures" *Am. J. Clin. Dermatol* 2000, 1(2), 81-88.

Yu et al., "Alpha-hydroxyacids and carboxylic acids" *Journal of Cosmetic Dermatology* 2004, 3, 76-87.

Peigang, Paula, *Take me to the cosmetics counter* Edition 1, p. 714, New World Publishing House, 2009.

*The most effective whitening essence course in the world.* Edition 1, Qiutong Beauty College, p. 104, Northern Women and Children Press, 2010.

Wang, Jianxin, *Cosmetics Plant Materials Encyclopedia* Edition 1, pp. 105-106, 233-234 & 390-391, China Textile Press, 2012.

"An Inch of Skin is Worth an Inch of Gold, Why are the Lady Skin Care Products So Expensice?", Anonymity, www.7192.com, pp. 1-2, website: http://www.7192.com/2017/0210/135254.shtml.

First Office Action from the China National Intellectual Property Administration (CNIPA) issued in corresponding Application No. 201610388122.1, dated Jun. 18, 2021.

Search Report from the China National Intellectual Property Administration (CNIPA) issued in corresponding Application No. 2016103881221, dated Jun. 10, 2021.

* cited by examiner

COSMETIC COMPOSITIONS

CROSS-REFERENCE TO RELATED APPLICATIONS

This application is a continuation of U.S. application Ser. No. 14/958,252, filed Dec. 3, 2015, which claims the benefit of U.S. Provisional Application No. 62/103,942, filed Jan. 15, 2015, and U.S. Provisional Application No. 62/086,790, filed Dec. 3, 2014. The contents of the referenced applications are incorporated into the present application by reference.

BACKGROUND OF THE INVENTION

1. Field of the Invention

The present invention relates generally to compositions and methods that can be used to improve the skin's visual appearance. In certain aspects, the compositions disclosed herein can include, for example, a combination of ingredients to exfoliate, reduce or eliminate irritation from exfoliation, renew the skin, increase skin radiance, sooth the skin, and/or increase skin smoothness.

2. Description of Related Art

Ageing, chronic exposure to adverse environmental factors, malnutrition, fatigue, etc., can change the visual appearance, physical properties, or physiological functions of skin in ways that are considered visually undesirable. The most notable and obvious changes include the development of fine lines and wrinkles, loss of elasticity, increased sagging, loss of firmness, loss of color evenness or tone, coarse surface texture, and mottled pigmentation. Less obvious but measurable changes which occur as skin ages or endures chronic environmental insult include a general reduction in cellular and tissue vitality, reduction in cell replication rates, reduced cutaneous blood flow, reduced moisture content, accumulated errors in structure and function, alterations in the normal regulation of common biochemical pathways, and a reduction in the skin's ability to remodel and repair itself. Many of the alterations in appearance and function of the skin are caused by changes in the outer epidermal layer of the skin, while others are caused by changes in the lower dermis.

Previous attempts to improve the visual appearance of skin with known skin active-ingredients have been shown to have various drawbacks such as skin irritation and prolonged recovery periods.

SUMMARY OF THE INVENTION

The inventors determined that a variety of compounds, compositions, and extracts have therapeutic benefits. In particular, the inventors identified a set of formulations that work to exfoliate, to decrease or eliminate skin irritation due to the exfoliation of the skin, to renew skin, and/or to increase skin radiance and/or smoothness. This results in products that have excellent exfoliating properties without some of the negative effects typically associated with exfoliating products and/or products that can reduce unwanted side effects of exfoliation of the skin. It has been determined that a set of formulations work together to provide activities that are not present in an individual ingredient of the formulation.

In this regard, there is disclosed compositions that include 4-tert-butylcyclohexanol, plankton extract, *Phragmites communis* extract, *Poria cocos* extract, *Cucurbita pepo* (pumpkin) seed extract, *Mucor miehei* extract, *Bacillus* ferment, *Opuntia coccinellifera* flower extract and/or hydrolyzed *Opuntia ficus-indica* flower extract. In particular aspects, compositions disclosed herein can include any one of, any combination of, all of, or at least 1, 2, 3, 4, 5, 6, 7, or 8 of said compounds, compositions, and extracts. In particular instances, the combination of 4-tert-butylcyclohexanol, plankton extract, *Phragmites communis* extract, *Poria cocos* extract, and *Cucurbita pepo* (pumpkin) seed extract worked especially well to reduce or eliminate irritation from exfoliation, renew skin, and/or increase skin radiance and smoothness. In another particular instance, the combination of *Mucor miehei* extract, *Bacillus* ferment, plankton extract, and *Opuntia coccinellifera* flower extract or hydrolyzed *Opuntia ficus-indica* flower extract worked especially well to exfoliate, reduce or eliminate irritation from exfoliation, renew skin, and/or increase skin radiance and smoothness. In another particular instance the above compositions worked well to reduce skin irritation due to skin exposure to an exfoliant, alpha hydroxy acid, or acids which may or may not be present in the composition. In yet another particular instance, the above compositions are components of a facial peel capable of exfoliating the skin.

In one instance, there is disclosed a topical skin composition that is capable of exfoliation, capable of reducing or eliminating irritation from exfoliation, capable of skin renewal, and/or capable of increasing skin radiance and/or smoothness comprising any of, a combination of, or all of water, triethanolamine, glycolic acid, glycerin, butylene glycol, sea water, cetearyl alcohol, arachidyl alcohol, sorbitan isostearate, dicaprylyl carbonate, biosaccharide gum-1, behenyl alcohol, hydroxyethyl acrylate/sodium acryloyldimethyltaurate copolymer, ammonium acryloyldimethyltaurate/VP copolymer, pentylene glycol, methyldihydrojasmonate, isohexadecane, Acacia senegal gum extract, cetearyl glucoside, arachidyl glucoside, 4-tert-butylcyclohexanol, magnesium aluminum silicate, dimethicone, ethylene brassylate, xanthan gum, ethyl linalool, polysorbate 60, disodium EDTA, titanium dioxide, plankton extract, *Phragmites communis* extract, *Poria cocos* extract, and/or *Cucurbita pepo* (pumpkin) seed extract. The amounts of the ingredients within the composition can vary. The concentrations of these ingredients can range from 0.00001 to 99% by weight or volume of the composition or any integer or range derivable therein as explained in other portions of this specification which are incorporated into this paragraph by reference. In one instance, the composition includes 25% to 80% w/w of water, 3% to 15% w/w triethanolamine, 2% to 20% w/w glycolic acid, 1% to 10% w/w glycerin, 1% to 10% w/w butylene glycol, 0.1% to 5% w/w sea water, 0.1% to 5% w/w cetearyl alcohol, 0.1% to 5% w/w arachidyl alcohol, 0.1% to 5% w/w sorbitan isostearate, 0.1% to 3% w/w dicaprylyl carbonate, 0.1% to 3% w/w biosaccharide gum-1, 0.1% to 3% w/w behenyl alcohol, 0.1% to 3% w/w hydroxyethyl acrylate/sodium acryloyldimethyltaurate copolymer, 0.1% to 3% w/w ammonium acryloyldimethyltaurate/VP copolymer, 0.1% to 3% w/w pentylene glycol, 0.1% to 3% w/w methyldihydrojasmonate, 0.1% to 3% w/w isohexadecane, 0.1% to 1.5% w/w acacia Senegal gum extract, 0.1% to 1.5% w/w cetearyl glucoside, 0.1% to 1.5% w/w arachidyl glucoside, 0.1% to 1.5% w/w 4-tert-butylcyclohexanol, 0.01% to 1% w/w magnesium aluminum silicate, 0.01% to 1% w/w dimethicone, 0.01% to 1% w/w ethylene brassylate, 0.01% to 1% w/w xanthan gum, 0.01% to 1% w/w ethyl linalool, 0.01% to 1% w/w polysorbate 60, 0.01% to 1% w/w disodium EDTA, 0.01% to 1% w/w titanium dioxide, 0.001% to 0.1% w/w plankton extract, 0.001% to 0.1% w/w *Phragmites communis* extract, 0.001% to 0.1% w/w *Poria cocos* extract, and/or 0.0001% to 0.01% w/w *Cucurbita pepo* (pumpkin) seed extract. In particular aspects, the concentration of water can be at least 35% to 80% by weight of water.

In another instance, there is disclosed a topical skin composition that is capable of exfoliation, capable of reducing or eliminating irritation from exfoliation, capable of skin renewal, and/or capable of increasing skin radiance and/or smoothness comprising any of, a combination of, or all of water, *Mucor miehei* extract, *Bacillus* ferment, plankton extract, *Opuntia coccinellifera* flower extract, and/or hydrolyzed *Opuntia ficus-indica* flower extract. In some instances, the composition further polysilicone-11; cyclopentasiloxane; dimethicone; glycerin; PEG-10 dimethicone; butylene glycol; bis-PEG-18 methyl ether dimethyl silane; phenoxyethanol; ammonium acryloyldimethyltaurate/VP copolymer; propylene glycol; biosaccharide gum-1; Acacia senegal gum extract; hydroxyethyl acrylate/sodium acryloyldimethyl taurate copolymer; squalene; decylene glycol; sodium citrate; hydroxyethylcellulose; 1,2-hexanediol; citric acid; dipotassium glycyrrhizate; tocopheryl acetate; xanthan gum; hydroxypropyl cyclodextrin; triethanolamine; polysorbate 60; disodium EDTA; sorbitan isostearate; and/or potassium sorbate. The concentrations of these ingredients can range from 0.00001 to 99% by weight or volume of the composition or any integer or range derivable therein as explained in other portions of this specification which are incorporated into this paragraph by reference. In particular aspects, the composition contains 40% to 60% w/w of water; 0.01% to 1% w/w of *Mucor miehei* extract; 0.001% to 1% w/w of *Bacillus* ferment; 0.001% to 0.1% w/w of plankton extract; 0.01% to 1% w/w of hydrolyzed *Opuntia ficus-indica* flower extract or *Opuntia coccinellifera* flower extract; 10% to 30% w/w of polysilicone-11; 5% to 20% w/w of cyclopentasiloxane; 1% to 10% w/w of dimethicone; 1% to 10% w/w of glycerin; 1% to 10% w/w of PEG-10 dimethicone; 0.5% to 5% w/w of butylene glycol; 0.5% to 5% w/w of bis-PEG-18 methyl ether dimethyl silane; 0.1% to 3% w/w of phenoxyethanol; 0.1% to 3% w/w of ammonium acryloyldimethyltaurate/VP copolymer; 0.1% to 3% w/w of propylene glycol; 0.1% to 3% w/w of biosaccharide gum-1; 0.1% to 1.5% w/w of Acacia senegal gum extract; 0.1% to 1.5% w/w of hydroxyethyl acrylate/sodium acryloyldimethyl taurate copolymer; 0.1% to 1.5% w/w of squalene; 0.01% to 1% w/w of decylene glycol; 0.01% to 1% w/w of sodium citrate; 0.01% to 1% w/w of hydroxyethylcellulose; 0.01% to 1% w/w of 1,2-hexanediol; 0.01% to 1% w/w of citric acid; 0.01% to 1% w/w of dipotassium glycyrrhizate; 0.01% to 1% w/w of tocopheryl acetate; 0.01% to 1% w/w of xanthan gum; 0.01% to 1% w/w of hydroxypropyl cyclodextrin; 0.01% to 1% w/w of triethanolamine; 0.01% to 1% w/w of polysorbate 60; 0.01% to 1% w/w of disodium EDTA; 0.001% to 0.1% w/w of sorbitan isostearate; and/or 0.001% to 0.1% w/w of potassium sorbate.

In particular aspects, the concentration of water can be at least 35% to 80% by weight of water. In some instances, the composition may further comprise adenosine. In some instances, the composition comprises 0.001% to 1% w/w of adenosine. In some instances, the composition may further comprise *Opuntia tuna* fruit extract. In some instances, the composition comprises 0.00001% to 0.01% w/w of *Opuntia tuna* fruit extract. In some instances, the composition may further comprise an alpha-hydroxy acid. In some instances, the alpha-hydroxy acid is glycolic acid. In some instances, the composition is an emulsion.

Also disclosed are methods of counteracting skin irritation caused by an exfoliant comprising topically applying any one of the compositions disclosed herein to skin in need thereof. In one instance, the skin irritation can be caused by an alpha hydroxy acid. In another aspect, a method is disclosed of exfoliating skin comprising topically applying any one of the compositions disclosed herein. It is also disclosed that any of the methods disclosed herein can further comprise applying the composition to a face.

Also disclosed are the following Embodiments 1 to 132 of the present invention. Embodiment 1 is a method of counteracting skin irritation caused by an exfoliant comprising topically applying a composition comprising: water; 4-tert-butylcyclohexanol; plankton extract; *Phragmites communis* extract; *Poria cocos* extract; and *Cucurbita pepo* (pumpkin) seed extract to skin in need thereof. Embodiment 2 is the method of Embodiment 1, wherein the composition comprises: 25% to 80% w/w of water; 0.1% to 1.5% w/w 4-tert-butylcyclohexanol; 0.001% to 0.1% w/w plankton extract; 0.001% to 0.1% w/w *Phragmites communis* extract; 0.001% to 0.1% w/w *Poria cocos* extract; and 0.0001% to 0.01% w/w *Cucurbita pepo* (pumpkin) seed extract. Embodiment 3 is the method of Embodiment 1, wherein the *Cucurbita pepo* (pumpkin) seed extract increases collagen production in the skin. Embodiment 4 is the method of Embodiment 1, wherein the *Cucurbita pepo* (pumpkin) seed extract inhibits MMP3 activity in skin. Embodiment 5 is the method of Embodiment 1, wherein the 4-tert-butylcyclohexanol reduces irritation of the skin. Embodiment 6 is the method of Embodiment 1, wherein the plankton extract conditions the skin. Embodiment 7 is the method of Embodiment 1, wherein the plankton extract reduces inflammation in the skin. Embodiment 8 is the method of Embodiment 1, wherein the *Phragmites communis* extract and *Poria cocos* extract reduces inflammation in the skin. Embodiment 9 is the method of Embodiment 1, wherein the *Phragmites communis* extract and *Poria cocos* extract increases skin barrier repair and/or skin barrier maintenance. Embodiment 10 is the method of Embodiment 1, wherein the composition is formulated as a facial peel. Embodiment 11 is the method of Embodiment 1, wherein the exfoliant is an alpha hydroxy acid. Embodiment 12 is the method of Embodiment 10, wherein the composition further comprises an exfoliant. Embodiment 13 is the method of Embodiment 12, wherein the exfoliant is an alpha hydroxy acid. Embodiment 14 is the method of Embodiment 13, wherein the composition comprises 2% to 20% w/w alpha hydroxy acid. Embodiment 15 is the method of Embodiment 14, wherein the alpha hydroxy acid is glycolic acid. Embodiment 16 is the method of Embodiment 1, further comprising applying the composition to a face. Embodiment 17 is a method of exfoliating skin comprising topically applying a composition comprising: water; 4-tert-butylcyclohexanol; plankton extract; *Phragmites communis* extract; *Poria cocos* extract; *Cucurbita pepo* (pumpkin) seed extract; and an exfoliant. Embodiment 18 is the method of Embodiment 17, wherein the composition comprises: 25% to 80% w/w of water; 0.1% to 1.5% w/w 4-tert-butylcyclohexanol; 0.001% to 0.1% w/w plankton extract; 0.001% to 0.1% w/w *Phragmites communis* extract; 0.001% to 0.1% w/w *Poria cocos* extract; and 0.0001% to 0.01% w/w *Cucurbita pepo* (pumpkin) seed extract. Embodiment 19 is the method of Embodiment 17, wherein the *Cucurbita pepo* (pumpkin) seed extract increases collagen production in the skin. Embodiment 20 is the method of Embodiment 17, wherein the *Cucurbita pepo* (pumpkin) seed extract inhibits MMP3 activity in skin. Embodiment 21 is the method of Embodiment 17, wherein the 4-tert-butylcyclohexanol reduces irritation of the skin. Embodiment 22 is the method of Embodiment 17, wherein the plankton extract conditions the skin. Embodiment 23 is the method of Embodiment 17, wherein the plankton extract reduces inflammation in the skin. Embodiment 24 is the method of Embodiment 17, wherein the *Phragmites communis* extract and *Poria cocos* extract reduces inflammation in the skin. Embodiment 25 is the method of Embodiment 17, wherein the *Phragmites communis* extract and *Poria cocos* extract increases skin barrier repair and/or skin barrier maintenance. Embodiment 26 is the method of Embodiment 17, wherein the composition is formulated as a facial peel. Embodiment 27 is the method of Embodiment 17, wherein the exfoliant is an alpha hydroxy acid. Embodiment 28 is the method of Embodiment 27, wherein the composition comprises 2% to 20% w/w alpha hydroxy acid. Embodiment 29 is the method of Embodiment 28, wherein the alpha hydroxy acid is glycolic acid. Embodiment 30 is the method of Embodiment 17, further comprising applying the composition to a face. Embodiment 31 is a method of increasing collagen production in skin comprising topically applying a composition comprising: water; 4-tert-butylcyclohexanol; plankton extract; *Phragmites communis* extract; *Poria cocos* extract; and *Cucurbita pepo* (pumpkin) seed extract wherein collagen production in skin is increased. Embodiment 32 is the method of Embodiment 31, wherein the composition comprises: 25% to 80% w/w of water; 0.1% to 1.5% w/w 4-tert-butylcyclohexanol; 0.001% to 0.1% w/w plankton extract; 0.001% to 0.1% w/w *Phragmites communis* extract; 0.001% to 0.1% w/w *Poria cocos* extract; and 0.0001% to 0.01% w/w *Cucurbita pepo* (pumpkin) seed extract. Embodiment 33 is the method of Embodiment 31, wherein the *Cucurbita pepo* (pumpkin) seed extract increases collagen production in the skin. Embodiment 34 is the method of Embodiment 31, wherein the *Cucurbita pepo* (pumpkin) seed extract inhibits MMP3 activity in skin. Embodiment 35 is the method of Embodiment 31, wherein the 4-tert-butylcyclohexanol reduces irritation of the skin. Embodiment 36 is the method of Embodiment 31, wherein the plankton extract conditions the skin. Embodiment 37 is the method of Embodiment 31, wherein the plankton extract reduces inflammation in the skin. Embodiment 38 is the method of Embodiment 31, wherein the *Phragmites communis* extract and *Poria cocos* extract reduces inflammation in the skin. Embodiment 39 is the method of Embodiment 31, wherein the *Phragmites communis* extract and *Poria cocos* extract increases skin barrier repair and/or skin barrier maintenance. Embodiment 40 is the method of Embodiment 31, wherein the composition is formulated as a facial peel. Embodiment 41 is the method of Embodiment 40, wherein the composition further comprises an exfoliant. Embodiment 42 is the method of Embodiment 41, wherein the exfoliant is an alpha hydroxy acid. Embodiment 43 is the method of Embodiment 42, wherein the composition comprises 2% to 20% w/w alpha hydroxy acid. Embodiment 44 is the method of Embodiment 43, wherein the alpha hydroxy acid is glycolic acid. Embodiment 45 is the method of Embodiment 31, further comprising applying the composition to a face. Embodiment 46 is a method of inhibiting MMP3 activity in skin comprising topically applying a composition comprising: water; 4-tert-butylcyclohexanol; plankton extract; *Phragmites communis* extract; *Poria cocos* extract; and *Cucurbita pepo* (pumpkin) seed extract wherein MMP3 activity is decreased in skin. Embodiment 47 is the method of Embodiment 46, wherein the composition comprises: 25% to 80% w/w of water; 0.1% to 1.5% w/w 4-tert-butylcyclohexanol; 0.001% to 0.1% w/w plankton extract; 0.001% to 0.1% w/w *Phragmites communis* extract; 0.001% to 0.1% w/w *Poria cocos* extract; and 0.0001% to 0.01% w/w *Cucurbita pepo* (pumpkin) seed extract. Embodiment 48 is the method of Embodiment 46, wherein the *Cucurbita pepo* (pumpkin) seed extract increases collagen production in the skin. Embodiment 49 is the method of Embodiment 46, wherein the *Cucurbita pepo* (pumpkin) seed extract inhibits MMP3 activity in skin. Embodiment 50 is the method of Embodiment 46, wherein the 4-tert-butylcyclohexanol reduces irritation of the skin. Embodiment 51 is the method of Embodiment 46, wherein the plankton extract conditions the skin. Embodiment 52 is the method of Embodiment 46, wherein the plankton extract reduces inflammation in the skin. Embodiment 53 is the method of Embodiment 46, wherein the *Phragmites communis* extract and *Poria cocos* extract reduces inflammation in the skin. Embodiment 54 is the method of Embodiment 46, wherein the *Phragmites communis* extract and *Poria cocos* extract increases skin barrier repair and/or skin barrier maintenance. Embodiment 55 is the method of Embodiment 46, wherein the composition is formulated as a facial peel. Embodiment 56 is the method of Embodiment 55, wherein the composition further comprises an exfoliant. Embodiment 57 is the method of Embodiment 56, wherein the exfoliants is an alpha hydroxy acid. Embodiment 58 is the method of Embodiment 57, wherein the composition comprises 2% to 20% w/w alpha hydroxy acid. Embodiment 59 is the method of Embodiment 58, wherein the alpha hydroxy acid is glycolic acid. Embodiment 60 is the method of Embodiment 46, further comprising applying the composition to a face. Embodiment 61 is a method of counteracting skin irritation caused by an exfoliant comprising topically applying a composition comprising: *Mucor miehei* extract; *Bacillus* ferment; plankton extract; and hydrolyzed *Opuntia ficus-indica* flower extract or *Opuntia coccinellifera* flower extract to skin in need thereof. Embodiment 62 is the method of Embodiment 61, wherein the composition comprises: 40% to 60% w/w of water; 0.01% to 1% w/w of *Mucor miehei* extract; 0.001% to 1% w/w of *Bacillus* ferment; 0.001% to 0.1% w/w of plankton extract; and 0.01% to 1% w/w of hydrolyzed *Opuntia ficus-indica* flower extract or *Opuntia coccinellifera* flower extract to skin in need thereof. Embodiment 63 is the method of Embodiment 61, wherein the composition further comprises 25 to 80% w/w of water. Embodiment 64 is the method of Embodiment 61, wherein the *Mucor miehei* extract exfoliates the skin. Embodiment 65 is the method of Embodiment 61, wherein the *Bacillus* ferment exfoliates the skin. Embodiment 66 is the method of Embodiment 61, wherein the plankton extract conditions the skin. Embodiment 67 is the method of Embodiment 61, wherein the plankton extract reduces inflammation in the skin. Embodiment 68 is the method of Embodiment 61, wherein the composition comprises hydrolyzed *Opuntia ficus-indica* flower extract and the hydrolyzed *Opuntia ficus-indica* flower extract exfoliates the skin. Embodiment 69 is the method of Embodiment 61, wherein the composition further comprises: adenosine. Embodiment 70 is the method of Embodiment 69, wherein the composition comprises 0.001% to 1% w/w of adenosine. Embodiment 71 is the method of Embodiment 61, wherein the composition further comprises: *Opuntia tuna* fruit extract. Embodiment 72 is the method of Embodiment 71, wherein the composition comprises 0.00001% to 0.01% w/w of *Opuntia tuna* fruit extract. Embodiment 73 is the method of Embodiment 61, wherein the composition is formulated as a facial peel. Embodiment 74 is the method of Embodiment 73, wherein the composition further comprises an alpha hydroxy acid. Embodiment 75 is the method of Embodiment 74, wherein the composition comprises 2% to 20% w/w alpha hydroxy acid. Embodiment 76 is the method of Embodiment 75, wherein the alpha hydroxy acid is glycolic acid. Embodiment 77 is the method of Embodiment 61, wherein the skin irritation is caused by an alpha hydroxy acid. Embodiment 78 is the method of Embodiment 61, wherein the composition is an emulsion. Embodiment 79 is the method of Embodiment 61, further comprising applying the composition to a face. Embodiment 80 is a method of exfoliating skin comprising topically applying a composition comprising: *Mucor miehei* extract; *Bacillus* ferment; plankton extract; and hydrolyzed *Opuntia ficus-indica* flower extract or *Opuntia coccinellifera* flower extract. Embodiment 81 is the method of Embodiment 80, wherein the composition comprises: 40% to 60% w/w of water; 0.01% to 1% w/w of *Mucor miehei* extract; 0.001% to 1% w/w of *Bacillus* ferment; 0.001% to 0.1% w/w of plankton extract; and 0.01% to 1% w/w of hydrolyzed *Opuntia ficus-indica* flower extract or *Opuntia coccinellifera* flower extract to skin in need thereof. Embodiment 82 is the method of Embodiment 80, wherein the composition further comprises 25 to 80% w/w of water. Embodiment 83 is the method of Embodiment 80, wherein the *Mucor miehei* extract exfoliates the skin. Embodiment 84 is the method of Embodiment 80, wherein the *Bacillus* ferment exfoliates the skin. Embodiment 85 is the method of Embodiment 80, wherein the plankton extract conditions the skin. Embodiment 86 is the method of Embodiment 80, wherein the plankton extract reduces inflammation in the skin. Embodiment 87 is the method of Embodiment 80, wherein the composition comprises hydrolyzed *Opuntia ficus-indica* flower extract and the hydrolyzed *Opuntia ficus-indica* flower extract exfoliates the skin. Embodiment 88 is the method of Embodiment 80, wherein the composition further comprises: adenosine. Embodiment 89 is the method of Embodiment 88, wherein the composition comprises 0.001% to 1% w/w of adenosine. Embodiment 90 is the method of Embodiment 80, wherein the composition further comprises: *Opuntia tuna* fruit extract. Embodiment 91 is the method of Embodiment 90, wherein the composition comprises 0.00001% to 0.01% w/w of *Opuntia tuna* fruit extract. Embodiment 92 is the method of Embodiment 80, wherein the composition is formulated as a facial peel. Embodiment 93 is the method of Embodiment 92, wherein the composition further comprises an alpha hydroxy acid. Embodiment 94 is the method of Embodiment 93, wherein the composition comprises 2% to 20% w/w alpha hydroxy acid. Embodiment 95 is the method of Embodiment 94, wherein the alpha hydroxy acid is glycolic acid. Embodiment 96 is the method of Embodiment 80, wherein the composition is an emulsion. Embodiment 97 is the method of Embodiment 80, further comprising applying the composition to a face. Embodiment 98 is a topical skin composition comprising: water; 4-tert-butylcyclohexanol; plankton extract; *Phragmites communis* extract; *Poria cocos* extract; and *Cucurbita pepo* (pumpkin) seed extract. Embodiment 99 is the topical skin composition of Embodiment 98, comprising 25% to 80% w/w of water; 0.1% to 1.5% w/w 4-tert-butylcyclohexanol; 0.001% to 0.1% w/w plankton extract; 0.001% to 0.1% w/w *Phragmites communis* extract; 0.001% to 0.1% w/w *Poria cocos* extract; and 0.0001% to 0.01% w/w *Cucurbita pepo* (pumpkin) seed extract. Embodiment 100 is the topical skin composition of Embodiment 98, further comprising: triethanolamine; glycerin; butylene glycol; sea water; cetearyl alcohol; arachidyl alcohol; sorbitan isostearate; dicaprylyl carbonate; biosaccharide gum-1; and behenyl alcohol. Embodiment 101 is the topical skin composition of Embodiment 100, comprising: 3% to 15% w/w triethanolamine; 1% to 10% w/w glycerin; 1% to 10% w/w butylene glycol; 0.1% to 5% w/w sea water; 0.1% to 5% w/w cetearyl alcohol; 0.1% to 5% w/w arachidyl alcohol; 0.1% to 5% w/w sorbitan isostearate; 0.1% to 3% w/w dicaprylyl carbonate; 0.1% to 3% w/w biosaccharide gum-1; and 0.1% to 3% w/w behenyl alcohol. Embodiment 102 is the topical skin composition of Embodiment 100, further comprising: hydroxyethyl acrylate/sodium acryloyldimethyltaurate copolymer; ammonium acryloyldimethyltaurate/VP copolymer; pentylene glycol; methyldihydrojasmonate; isohexadecane; acacia Senegal gum extract; cetearyl glucoside; arachidyl glucoside; magnesium aluminum silicate; dimethicone; ethylene brassylate; xanthan gum; ethyl linalool; polysorbate 60; disodium EDTA; and titanium dioxide. Embodiment 103 is the topical skin composition of Embodiment 102, comprising: 0.1% to 3% w/w hydroxyethyl acrylate/sodium acryloyldimethyltaurate copolymer; 0.1% to 3% w/w ammonium acryloyldimethyltaurate/VP copolymer; 0.1% to 3% w/w pentylene glycol; 0.1% to 3% w/w methyldihydrojasmonate; 0.1% to 3% w/w isohexadecane; 0.1% to 1.5% w/w acacia Senegal gum extract; 0.1% to 1.5% w/w cetearyl glucoside; 0.1% to 1.5% w/w arachidyl glucoside; 0.01% to 1% w/w magnesium aluminum silicate; 0.01% to 1% w/w dimethicone; 0.01% to 1% w/w ethylene brassylate; 0.01% to 1% w/w xanthan gum; 0.01% to 1% w/w ethyl linalool; 0.01% to 1% w/w polysorbate 60; 0.01% to 1% w/w disodium EDTA; and 0.01% to 1% w/w titanium dioxide. Embodiment 104 is the topical skin composition of Embodiment 98, wherein the composition is capable of counteracting skin irritation caused by an exfoliant. Embodiment 105 is the topical skin composition of Embodiment 104, wherein the composition is capable of counteracting skin irritation caused by an alpha hydroxy acid. Embodiment 106 is the topical skin composition of Embodiment 98, wherein the composition is formulated as a facial peel. Embodiment 107 is the topical skin composition of Embodiment 106, further comprising an exfoliant. Embodiment 108 is the topical skin composition of Embodiment 107, wherein the exfoliants is an alpha hydroxy acid. Embodiment 109 is the topical skin composition of Embodiment 108, comprising 2% to 20% w/w alpha hydroxy acid. Embodiment 110 is the topical skin composition of Embodiment 109, wherein the alpha hydroxy acid is glycolic acid. Embodiment 111 is the topical skin composition of Embodiment 98, wherein the composition is capable of increasing collagen production in skin. Embodiment 112 is the topical skin composition of Embodiment 98, wherein the composition is capable of inhibiting MMP3 activity in skin. Embodiment 113 is a topical skin composition comprising: *Mucor miehei* extract; *Bacillus* ferment; plankton extract; and hydrolyzed *Opuntia ficus-indica* flower extract or *Opuntia coccinellifera* flower extract. Embodiment 114 is the topical skin composition of Embodiment 113, wherein the composition comprises: 40% to 60% w/w of water; 0.01% to 1% w/w of *Mucor miehei* extract; 0.001% to 1% w/w of *Bacillus* ferment; 0.001% to 0.1% w/w of plankton extract; and 0.01% to 1% w/w of hydrolyzed *Opuntia ficus-indica* flower extract or *Opuntia coccinellifera* flower extract to skin in need thereof. Embodiment 115 is the topical skin composition of Embodiment 113, further comprising: polysilicone-11; cyclopentasiloxane; dimethicone; glycerin; PEG-10 dimethicone; butylene glycol; and bis-PEG-18 methyl ether dimethyl silane. Embodiment 116 is the topical skin composition of Embodiment 115, comprising: 10% to 30% w/w of polysilicone-11; 5% to 20% w/w of cyclopentasiloxane; 1% to 10% w/w of dimethicone; 1% to 10% w/w of glycerin; 1% to 10% w/w of PEG-10 dimethicone; 0.5% to 5% w/w of butylene glycol; and 0.5% to 5% w/w of bis-PEG-18 methyl ether dimethyl silane. Embodiment 117 is the topical skin composition of Embodiment 115, further comprising: phenoxyethanol; ammonium acryloyldimethyltaurate/VP copolymer; propylene glycol; biosaccharide gum-1; Acacia senegal gum extract; hydroxyethyl acrylate/sodium acryloyldimethyl taurate copolymer; squalene; decylene glycol; sodium citrate; hydroxyethylcellulose; 1,2-hexanediol; citric acid; dipotassium glycyrrhizate; tocopheryl acetate; and xanthan gum. Embodiment 118 is the topical skin composition of Embodiment 117, comprising: 0.1% to 3% w/w of phenoxyethanol; 0.1% to 3% w/w of ammonium acryloyldimethyltaurate/VP copolymer; 0.1% to 3% w/w of propylene glycol; 0.1% to 3% w/w of biosaccharide gum-1; 0.1% to 1.5% w/w of Acacia senegal gum extract; 0.1% to 1.5% w/w of hydroxyethyl acrylate/sodium acryloyldimethyl taurate copolymer; 0.1% to 1.5% w/w of squalene; 0.01% to 1% w/w of decylene glycol; 0.01% to 1% w/w of sodium citrate; 0.01% to 1% w/w of hydroxyethylcellulose; 0.01% to 1% w/w of 1,2-hexanediol; 0.01% to 1% w/w of citric acid; 0.01% to 1% w/w of dipotassium glycyrrhizate; 0.01% to 1% w/w of tocopheryl acetate; and 0.01% to 1% w/w of xanthan gum. Embodiment 119. The topical skin composition of Embodiment 117, further comprising: hydroxypropyl cyclodextrin; triethanolamine; polysorbate 60; disodium EDTA; sorbitan isostearate; and potassium sorbate. Embodiment 120. The topical skin composition of Embodiment 119, comprising: 0.01% to 1% w/w of hydroxypropyl cyclodextrin; 0.01% to 1% w/w of triethanolamine; 0.01% to 1% w/w of polysorbate 60; 0.01% to 1% w/w of disodium EDTA; 0.001% to 0.1% w/w of sorbitan isostearate; and 0.001% to 0.1% w/w of potassium sorbate. Embodiment 121 is the topical skin composition of Embodiment 113, comprising 25 to 80% w/w of water. Embodiment 122 is the topical skin composition of Embodiment 113, further comprising: adenosine. Embodiment 123 is the method of Embodiment 122, wherein the composition comprises 0.001% to 1% w/w of adenosine. Embodiment 124 is the method of Embodiment 113, wherein the composition further comprises: *Opuntia tuna* fruit extract. Embodiment 125 is the method of Embodiment 124, wherein the composition comprises 0.00001% to 0.01% w/w of *Opuntia tuna* fruit extract. Embodiment 126 is the topical skin composition of Embodiment 113, wherein the composition is capable of counteracting skin irritation caused by an exfoliant. Embodiment 127 is the topical skin composition of Embodiment 126, wherein the composition is capable of counteracting skin irritation caused by an alpha hydroxy acid. Embodiment 128 is the topical skin composition of Embodiment 113, wherein the composition is formulated as a facial peel. Embodiment 129 is the topical skin composition of Embodiment 128, further comprising an alpha hydroxy acid. Embodiment 130 is the topical skin composition of Embodiment 129, comprising 2% to 20% w/w alpha hydroxy acid. Embodiment 131 is the topical skin composition of Embodiment 130, wherein the alpha hydroxy acid is glycolic acid. Embodiment 132 is the topical skin composition of Embodiment 113, wherein the composition is an emulsion.

Any of the compositions can remain on the skin after topical application for 30 seconds, 1, 2, 3, 4, 5, 6, 7, 8, 9, 10, 15, 20, 30, 40, 50, or 60 minutes or more. The skin in need of the composition can be skin having a fine line or wrinkle or uneven skin. Uneven skin can be skin having hyperpigmented skin, melasmic skin, liver spots, dark spots, aged spots, brown spots, and the like. The skin, after the composition has been applied, can be protected from becoming irritated, reddened, dry, flaky, or cracked. Protection includes a reduced likelihood of skin developing said symptoms after using a/the skin exfoliating composition.

In particular aspects, compositions disclosed herein are formulated as topical skin composition. The composition can have a dermatologically acceptable vehicle or carrier for the compounds, compositions, and extracts. The composition can further include a moisturizing agent or a humectant, a surfactant, a silicone containing compounds, a UV agent, an oil, a non-naturally occurring compound, and/or other ingredients identified in this specification or those known in the art. The composition can include additional non-naturally occurring ingredients. The composition can be a lotion, cream, gel, serum, emulsion (e.g., oil-in-water, water-in-oil, silicone-in-water, water-in-silicone, water-in-oil-in-water, oil-in-water, oil-in-water-in-oil, oil-in-water-in-silicone, etc.), solutions (e.g., aqueous or hydro-alcoholic solutions), anhydrous bases (e.g., lipstick or a powder), ointments, milk, paste, aerosol, solid forms, eye jellies, etc. The composition can be in powdered form (e.g., dried, lyophilized, particulate, etc.). The composition can be formulated for topical skin application at least 1, 2, 3, 4, 5, 6, 7, or more times a day during use. In other aspects disclosed herein, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, cps, etc., as measured on a Brookfield Viscometer using a TC spindle at 2.5 rpm at 25° C.).

In particular instances, the extracts in the composition can be from the whole organism or plant and can be aqueous extracts. However, it is contemplated that in addition to the whole organism or plant, part of the organism or plant (e.g., root, bark, sap, stem, leaf, flower, seed, leaf, stem, root, flower, seed, sap, bark, etc.) can be used such that one portion of the organism or plant is used at the exclusion of the other portions of the organism or plant to produce the extract. As noted above, the extract can be an aqueous extract but can also be a non-aqueous extract. The extract can be extracted with alcohol (e.g., methanol, ethanol propanol, butanol, etc.), glycols (e.g., butylene glycol, propylene glycol, etc.), oils, water, etc. The extracts can contain parts, chemicals, etc., that are not naturally found together, or are not naturally found together at the ratios or concentrations found in nature. The extracts can be included in compositions such as topical skin compositions, edible compositions, injectable compositions, oral compositions, pharmaceutical compositions, hair care compositions, etc. The composition can include 0.0001% to 20% by weight of said organism or plant, organism part or plant part, and/or extract thereof (or 0.001, 0.01, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 30, 40, 50, 60, 70, 80, 90, 99%, or more or any integer or range therein).

The compositions disclosed herein can also be modified to have a desired oxygen radical absorbance capacity (ORAC)

value. In certain non-limiting aspects, the compositions disclosed herein or the plant, plant parts, or extracts thereof identified throughout this specification can be modified to have an ORAC value per mg of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 95, 100, 200, 300, 400, 500, 600, 700, 800, 900, 1000, 2000, 3000, 4000, 5000, 6000, 7000, 8000, 9000, 10000, 15000, 20000, 30000, 50000, 100000 or more or any range derivable therein.

The compositions in non-limiting aspects can have a pH of about 6 to about 9. In other aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In certain aspects, the triglyceride is a medium chain triglyceride (e.g., caprylic capric triglyceride). The compositions can also include preservatives. Non-limiting examples of preservatives include methylparaben, propylparaben, or a mixture of methylparaben and propylparaben.

The compositions disclosed herein can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, a non-naturally occurring compound, or an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

Kits that include the compositions disclosed herein are also contemplated. In certain embodiments, the composition is comprised in a container. The container can be a bottle, dispenser, or package. The container can dispense a predetermined amount of the composition. In certain aspects, the compositions is dispensed in a spray, dollop, or liquid. The container can include indicia on its surface. The indicia can be a word, an abbreviation, a picture, or a symbol.

It is also contemplated that the compositions disclosed throughout this specification can be used as a leave-on or rinse-off composition. By way of example, a leave-on composition can be one that is topically applied to skin and remains on the skin for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or overnight or throughout the day). Alternatively, a rinse-off composition can be a product that is intended to be applied to the skin and then removed or rinsed from the skin (e.g., with water) within a period of time such as less than 5, 4, 3, 2, or 1 minute. An example of a rinse of composition can be a skin cleanser, shampoo, conditioner, or soap. An example of a leave-on composition can be a skin moisturizer, sunscreen, mask, overnight cream, or a day cream.

It is contemplated that any embodiment discussed in this specification can be implemented with respect to any method or composition of the invention, and vice versa. Furthermore, compositions disclosed herein can be used to achieve methods of the invention.

In one embodiment, compositions disclosed herein can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

"Topical application" means to apply or spread a composition onto the surface of lips or keratinous tissue. "Topical skin composition" includes compositions suitable for topical application on lips or keratinous tissue. Such compositions are typically dermatologically-acceptable in that they do not have undue toxicity, incompatibility, instability, allergic response, and the like, when applied to lips or skin. Topical skin care compositions disclosed herein can have a selected viscosity to avoid significant dripping or pooling after application to skin.

"Keratinous tissue" includes keratin-containing layers disposed as the outermost protective covering of mammals and includes, but is not limited to, lips, skin, hair and nails.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase or production of a protein or molecule (e.g., matrix proteins such as fibronectin, laminin, collagen, or elastin or molecules such as hyaluronic acid) to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the transitional phase "consisting essentially of," in one non-limiting aspect, a basic and novel characteristic of the compositions and methods disclosed in this specification includes the compositions' abilities to reduce or prevent symptoms associated with sensitive skin (e.g., erythema) from appearing on a user's skin.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

In particular embodiments, any one of the following can be used or any combination thereof: 4-tert-butylcyclohexanol, plankton extract, *Phragmites communis* extract, *Poria cocos* extract, *Cucurbita pepo* (pumpkin) seed extract, *Mucor miehei* extract, *Bacillus* ferment, and *Opuntia coccinellifera* flower extract or hydrolyzed *Opuntia ficus-indica* flower extract. This combination of ingredients can be included in a wide-range of product formulations (e.g., serums, eye creams, toners, gels, masks, peels, etc.).

As noted above, several of the unique aspects of the present invention disclosed herein are to exfoliate skin, to eliminating skin irritation due to the exfoliation of the skin after or during exfoliation, to renew skin, and/or to increases skin radiance and/or smoothness. This allows for the benefits of skin exfoliation (which can reduce the appearance of fine lines and wrinkles and even skin tone by removing unwanted spots such as melasma, hyperpigmented skin, age spots, liver spots, dark spots, and the like) while reducing some unwanted side effects.

The following subsections describe non-limiting aspects of the present invention in further detail.

A. Exfoliating and Repairing Compositions

A particular exfoliating composition disclosed herein is designed to work to decrease or eliminate skin irritation due to the exfoliation of the skin, exfoliate skin while decreasing or eliminating skin irritation due to the exfoliation of the skin, to renew skin, and/or to increasing skin radiance and/or smoothness. The composition relies on a unique combination of 4-tert-butylcyclohexanol, plankton extract, *Phragmites communis* extract, *Poria cocos* extract, and/or *Cucurbita pepo* (pumpkin) seed extract. An example of such a composition is provided in Example 1, Table 1 and Table 2. While glycolic acid may be used as the active skin exfoliation ingredient, other acids and other exfoliation ingredients can also be used (e.g. lactic acid, citric acid, enzyme exfoliants, etc.).

Another particular exfoliating composition disclosed herein is designed to decrease or eliminate skin irritation due to the exfoliation of the skin, exfoliate skin while decreasing or eliminating skin irritation due to the exfoliation of the skin, to renew skin, and/or to increasing skin radiance and/or smoothness. The composition relies on a unique combination of *Mucor miehei* extract, *Bacillus* ferment, plankton extract, hydrolyzed *Opuntia ficus-indica* flower extract, and/or *Opuntia coccinellifera* flower extract. An example of such a composition is provided in Example 1, Table 3 and Table 4. While *Bacillus* ferment may be used as an active skin exfoliation ingredient, glycolic acid or other acids and other exfoliation ingredients can also be used (e.g. lactic acid, citric acid, enzyme exfoliants, etc.).

A particular repair composition disclosed herein is designed to work to decrease or eliminate skin irritation due to the exfoliation of the skin, to renew skin, and/or to increase skin radiance and/or smoothness. The composition relies on a unique combination of *Mucor miehei* extract, *Bacillus* ferment, plankton extract, hydrolyzed *Opuntia ficus-indica* flower extract, and/or *Opuntia coccinellifera* extract with or without an additional ingredient that is capable of exfoliating skin. An example of such a composition is provided in Example 1, Table 3 and Table 4.

4-tert-butylcyclohexanol is an organic compound that conforms to the formula:

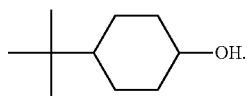

It is an anti-irritant agent useful for reducing burning and stinging of skin. It is commercially available from a wide range of sources (see International Cosmetic Ingredient Dictionary and Handbook, 12$^{th}$ edition, volume 1, page 331 (2008), which is incorporated by reference).

Plankton extract is an extract obtained from marine biomass. It is known to be a skin conditioner. It may also provide fatty acids, antioxidants, and zinc to the skin as well as reducing inflammation in the skin and protecting the skin from the sun. Plankton extract can be purchased from Barnet Products Corp. (USA) under the trade name Benoitine. In some embodiments, plankton extract is an exopolysaccharide synthesized by a micro-organism called *Vibrio alginolyticus* and belonging to the family of Thalassoplankton. In some embodiments, plankton extract is saccharide isomerate, an exopolysaccharide synthesized by a *Vibrio alginolyticus*. In some embodiments this ingredient is commercially available, e.g., from Barnet, which provides saccharide isomerate under the trade name Benoiderm.

*Phragmites communis* extract and *Poria cocos* helps to reduce skin inflammation. It has barrier repair and barrier maintenance functions and helps the skin become less reactive to external attacks. It is supplied by Chemisches Laboratorium (CLR) (Germany) under the trade name Syri-Calm™ CLR.

*Cucurbita pepo* (pumpkin) seed extract, extract from pumpkin seeds, can be purchased from Draco Natural Products Inc. (USA) under the trade name PUMPKIN EXTRACT™, Naturex (USA) under the trade name PUMPKIN SEED GLYCOLIC EXTRACT™, from Greentech S.A. (France) under the trade names ARP100™ and ARP 100™ Huileux, or from Soliance (France) under the trade name Ocaline PF.

*Mucor miehei* extract can be purchased from Active Organics (USA) under the trade name Actizyme™ E3M-M. In some embodiments, the *Mucor miehei* extract is a mushroom derived, water soluble enzyme of the aspartyl dependent, or acid protease class. In some embodiments, the *Mucor miehei* extract can exfoliate skin.

*Bacillus* ferment can be purchased from Sederma (France) under the trade name Keratoline™. In some embodiments, the *Bacillus* ferment is a ferment of *Bacillus subtilis*. In some embodiments, the *Bacillus* ferment can exfoliate skin.

Hydrolyzed *Opuntia ficus-indica* flower extract can be purchased from SiLab (France) under the trade name Exfolactive™ EL PX. In some embodiments, the hydrolyzed *Opuntia ficus-indica* flower extract can exfoliate skin.

*Opuntia coccinellifera* flower extract is an extract of the flower of the *Opuntia coccinellifera*. In some embodiments, the extract can condition the skin.

Adenosine is a heterocyclic organic compound generally conforming to the following structure:

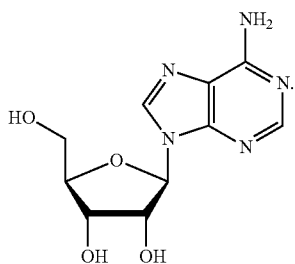

Adenosine is commercially available from a wide range of sources (see International Cosmetic Ingredient Dictionary and Handbook, 12th edition, volume 1, page 60 (2008), which is incorporated by reference).

The above exfoliating and repair compositions can be applied to the skin and remain on the skin for a period of time (e.g., at least 1, 2, 3, 4, 5, 10, 20, 30, or 60 minutes or more). After which, the composition, if needed, can be rinsed from the skin or peeled from the skin.

C. Amounts of Ingredients

It is contemplated that the compositions disclosed herein can include any amount of the ingredients discussed in this specification. The compositions can also include any number of combinations of additional ingredients described throughout this specification (e.g., pigments, or additional cosmetic or pharmaceutical ingredients). The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

D. Vehicles

The compositions disclosed herein can be incorporated into all types of vehicles. Non-limiting examples include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, and ointments. Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product.

E. Additional Ingredients

In addition to the combination of ingredients disclosed by the inventors, the compositions can also include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as para-aminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. aloe vera, chamomile, cucumber extract, *Ginkgo biloba*, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, methyl gluceth-20, and mannitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, biosaccharide gum-1, ethylhexylglycerin, pentylene glycol, hydrogenated polydecene, octyldodecyl oleate, and dipotassium glycyrrhizate). Non-limiting examples of some of these ingredients are provided in the following subsections.

a. UV Absorption Agents

UV absorption agents that can be used in combination with the compositions disclosed herein include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene di camphor sulfonic acid, di sodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidene camphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions disclosed herein include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrrolidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, aloe barbadensis, aloe-barbadensis extract, aloe barbadensis gel, *Althea officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamom (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystear-ate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*)oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera biennis*) oil, fatty acids, *Geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, *glycine*, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, *Macadamia ternifolia* nut oil, maltitol, *Matricaria* (*Chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus Aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*Mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

c. Antioxidants

Non-limiting examples of antioxidants that can be used with the compositions disclosed herein include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions disclosed herein can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects disclosed herein, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, e.g. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, e.g. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

g. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (e.g., extraction by using fat), maceration, solvent extraction, or mechanical pressing). When these types of oils are exposed to air they tend to evaporate (e.g., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, *macadamia* nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *Eucalyptus* oil, fennel oil, sea fennel oil, frankincense oil, *geranium* oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

h. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions disclosed herein. In certain aspects disclosed herein, thickeners include hydrogenated polyisobutene, trihydroxystearin, ammonium acryloyldimethyltaurate/vp copolymer, or a mixture of them.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, and mixtures thereof.

i. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

2. Pharmaceutical Ingredients

Pharmaceutical active agents are also contemplated as being useful with the compositions disclosed herein. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antip soriatic agents, anti seborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

F. Kits

Kits are also contemplated as being used in certain aspects of the present invention. For instance, compositions disclosed herein can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate some embodiments/instances of the present invention. It should be appreciated by those of skill in the art that the techniques disclosed in the examples which follow represent techniques determined by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Formulations having the ingredients from Example 1 were prepared as facial peels. The formulation in Table 1, Table 2, and Table 3 were prepared as an exfoliating peel. The formulation in Table 4 was prepared as a repairing or an exfoliating peel.

TABLE 1

| Ingredient | % Concentration (by weight) |
|---|---|
| water | 63.7 |
| triethanolamine | 8.75 |
| glycolic acid | 8 |
| glycerin | 3 |
| butylene glycol | 2 |
| sea water | 1.7 |
| cetearyl alcohol | 1.6 |
| arachidyl alcohol | 1.4 |
| sorbitan isostearate | 1 |
| dicaprylyl carbonate | 1 |
| biosaccharide gum-1 | 1 |
| behenyl alcohol | 0.75 |
| hydroxyethyl acrylate/sodium acryloyldimethyltaurate copolymer | 0.75 |
| ammonium acryloyldimethyltaurate/VP copolymer | 0.7 |
| pentylene glycol | 0.7 |
| methyldihydrojasmonate | 0.55 |
| isohexadecane | 0.5 |
| acacia Senegal gum extract | 0.4 |
| cetearyl glucoside | 0.4 |
| arachidyl glucoside | 0.4 |
| 4-tert-butylcyclohexanol | 0.3 |
| magnesium aluminum silicate | 0.2 |
| dimethicone | 0.2 |
| ethylene brassylate | 0.2 |
| xanthan gum | 0.15 |
| ethyl linalool | 0.15 |
| polysorbate 60 | 0.1 |
| disodium EDTA | 0.1 |
| titanium dioxide | 0.1 |

TABLE 1-continued

| Ingredient | % Concentration (by weight) |
|---|---|
| plankton extract | 0.01 |
| Phragmites communis extract | 0.01 |
| Poria cocos extract | 0.01 |
| Cucurbita pepo (pumpkin) seed extract | 0.002 |
| Excipients** | q.s. |

**Excipients were added to modify the rheological properties of the composition. Alternatively, the amount of water can be varied so long as the amount of water in the composition is at least 45% w/w, and preferably between 50 to 75% w/w.

TABLE 2

| Ingredient | % Concentration (by weight) |
|---|---|
| water | 72.3 |
| triethanolamine | 5 |
| glycolic acid | 4 |
| glycerin | 3 |
| butylene glycol | 2 |
| sea water | 1.7 |
| cetearyl alcohol | 1.6 |
| arachidyl alcohol | 1.4 |
| sorbitan isostearate | 1 |
| dicaprylyl carbonate | 1 |
| biosaccharide gum-1 | 1 |
| behenyl alcohol | 0.75 |
| hydroxyethyl acrylate/sodium acryloyldimethyltaurate copolymer | 0.3 |
| ammonium acryloyldimethyltaurate/VP copolymer | 0.7 |
| pentylene glycol | 0.7 |
| methyldihydrojasmonate | 0.55 |
| isohexadecane | 0.2 |
| acacia Senegal gum extract | 0.4 |
| cetearyl glucoside | 0.4 |
| arachidyl glucoside | 0.4 |
| 4-tert-butylcyclohexanol | 0.3 |
| magnesium aluminum silicate | 0.2 |
| dimethicone | 0.2 |
| ethylene brassylate | 0.2 |
| xanthan gum | 0.15 |
| ethyl linalool | 0.15 |
| disodium EDTA | 0.1 |
| titanium dioxide | 0.1 |
| polysorbate 60 | 0.04 |
| plankton extract | 0.01 |
| Phragmites communis extract | 0.01 |
| Poria cocos extract | 0.01 |
| Cucurbita pepo (pumpkin) seed extract | 0.002 |
| Excipients** | q.s. |

**Excipients were added to modify the rheological properties of the composition. Alternatively, the amount of water can be varied so long as the amount of water in the composition is at least 60% w/w, and preferably between 70 to 80% w/w.

TABLE 3

| Ingredient | % Concentration (by weight) |
|---|---|
| water | 49.4 |
| polysilicone-11 | 20 |
| cyclopentasiloxane | 9 |
| dimethicone | 5 |
| glycerin | 4 |
| PEG-10 dimethicone | 3 |
| butylene glycol | 2 |
| bis-PEG-18 methyl ether dimethyl silane | 2 |
| phenoxyethanol | 0.9 |
| ammonium acryloyldimethyltaurate/VP copolymer | 0.7 |
| propylene glycol | 0.5 |
| biosaccharide gum-1 | 0.5 |
| Acacia senegal gum extract | 0.4 |
| hydroxyethyl acrylate/sodium acryloyldimethyl taurate copolymer | 0.4 |
| squalane | 0.3 |
| decylene glycol | 0.2 |

TABLE 3-continued

| Ingredient | % Concentration (by weight) |
| --- | --- |
| *Mucor miehei* extract | 0.2 |
| sodium citrate | 0.2 |
| hydroxyethylcellulose | 0.15 |
| *Opuntia coccinellifera* flower extract and/or hydrolyzed *Opuntia ficus-indica* flower extract | 0.14 |
| 1,2-hexanediol | 0.12 |
| citric acid | 0.11 |
| dipotassium glycyrrhizate | 0.1 |
| tocopheryl acetate | 0.1 |
| xanthan gum | 0.1 |
| hydroxypropyl cyclodextrin | 0.07 |
| bacillus ferment | 0.07 |
| triethanolamine | 0.06 |
| polysorbate 60 | 0.06 |
| disodium EDTA | 0.05 |
| adenosine | 0.04 |
| sorbitan isostearate | 0.02 |
| potassium sorbate | 0.01 |
| saccharide isomerate | 0.01 |
| *Opuntia tuna* fruit extract (optional) | 0.0005 |
| Excipients** | q.s. |

**Excipients were added to modify the rheological properties of the composition. Alternatively, the amount of water can be varied so long as the amount of water in the composition is at least 40% w/w, and preferably between 45 to 65% w/w.

| Ingredient |
| --- |
| water |
| *Mucor miehei* extract |
| bacillus ferment |
| plankton extract |
| hydrolyzed *Opuntia ficus-indica* flower extract |
| glycolic acid (optional) |
| Excipients** |

**Excipients were added to modify the rheological properties of the composition. Alternatively, the amount of water can be varied so long as the amount of water in the composition is at least 15% w/w, and preferably between 25 to 85% w/w.

Example 2

Increase Dermal Matrix Proteins Present in Dermal/Epidermal Junction:

The skin contains constricting bands of connective tissue composed of matrix-producing fibroblasts, fat-producing adipocytes and the blood network. Connective tissue can vary in thickness and is held in place by a network of fibers that provides cushion for muscles and organs. This cushion or extracellular matrix is primarily composed of collagen to help provide support and foundation for the skin. When the dermis is strong and structurally sound, fat cells are unable to break through and become visible on the skin surface. The Applicants have determined that extracts of *Cucurbita pepo* seed can increase collagen production and inhibit an enzyme that degrades many types of collagen. Ocaline PF was used in the compositions of the Examples.

Collagen is the most predominant protein in the connective tissue. It is secreted by fibroblasts where it is matured by other proteins. Extracts of *Cucurbita pepo* seed increased the production of collagen I by 41.6% secreted by human fibroblasts compared to untreated controls.

Matrix proteins are degraded in the connective tissue by enzymes known as matrix metalloproteinases (MMPs), a group of zinc dependent enzymes (endopeptidases). MMPs are not constitutively expressed in the skin but their activity can be regulated. These enzymes degrade the extracellular matrix in a specific manner; different MMPs degrade specific matrix proteins. Many of the collagen found in the skin (Collagens I, III, IV, and VII) are targets of MMP-3 (Stromelysin 1). Inhibition of the enzyme's activity prevents the destruction of matrix proteins which are essential for the structural foundation of the skin. Extracts of *Cucurbita pepo* seeds inhibited >90% of the activity from purified MMP-3 enzyme.

Example 3

Additional Assays

Additional assays that can be used to determine the efficacy of any one of the ingredients or any combination of ingredients or compositions having said combination of ingredients disclosed throughout the specification and claims can be determined by methods known to those of ordinary skill in the art. The following are non-limiting assays that can be used in the context of the present invention. It should be recognized that other testing procedures can be used, including, for example, objective and subjective procedures.

B16 Pigmentation Assay:

Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilizes B16-F1 melanocytes (ATCC), an immortalized mouse melanoma cell line, to analyze the effect of compounds on melanogenesis. The endpoint of this assay is a spectrophotometric measurement of melanin production and cellular viability. B16-F1 melanocytes, can be cultivated in standard DMEM growth medium with 10% fetal bovine serum (Mediatech) at 37° C. in 10% $CO_2$ and then treated with any one of the active ingredients, combination of ingredients, or compositions having said combinations disclosed in the specification for 6 days. Following incubation, melanin secretion was measured by absorbance at 405 nm and cellular viability was quantified.

Collagen Stimulation Assay:

Collagen is an extracellular matrix protein critical for skin structure. Increased synthesis of collagen helps improve skin firmness and elasticity. This bioassay can be used to examine the effect of any one of the active ingredients, combination of ingredients, or compositions having said combinations disclosed in the specification on the production of procollagen peptide (a precursor to collagen) by human epidermal fibroblasts. The endpoint of this assay is a spectrophotometric measurement that reflects the presence of procollagen peptide and cellular viability. The assay employs the quantitative sandwich enzyme immunoassay technique whereby a monoclonal antibody specific for procollagen peptide has been pre-coated onto a microplate. Standards and samples can be pipetted into the wells and any procollagen peptide present is bound by the immobilized antibody. After washing away any unbound substances, an enzyme-linked polyclonal antibody specific for procollagen peptide can be added to the wells. Following a wash to remove any unbound antibody-enzyme reagent, a substrate solution can be added to the wells and color develops in proportion to the amount of procollagen peptide bound in the initial step using a microplate reader for detection at 450 nm. The color development can be stopped and the intensity of the color can be measured. Subconfluent normal human adult epidermal fibroblasts (Cascade Biologics) cultivated in standard DMEM growth medium with 10% fetal bovine serum (Mediatech) at 37° C. in 10% $CO_2$, can be treated with each of the combination of ingredients or compositions having said combinations disclosed in the specification for 3 days. Following incubation, cell culture medium can be collected and the amount of procollagen peptide secretion quantified using a sandwich enzyme linked immuno-sorbant assay (ELISA) from Takara (#MK101).

Tumor Necrosis Factor Alpha (TNF-α) Assay:

The prototype ligand of the TNF superfamily, TNF-α, is a pleiotropic cytokine that plays a central role in inflammation. Increase in its expression is associated with an up regulation in pro-inflammatory activity. This bioassay can be used to analyze the effect of any one of the active ingredients, combination of ingredients, or compositions having said combinations disclosed in the specification on the production of TNF-α by human epidermal keratinocytes. The endpoint of this assay can be a spectrophotometric measurement that reflects the presence of TNF-α and cellular viability. The assay employs the quantitative sandwich enzyme immunoassay technique whereby a monoclonal antibody specific for TNF-α has been pre-coated onto a microplate. Standards and samples can be pipetted into the wells and any TNF-α present is bound by the immobilized antibody. After washing away any unbound substances, an enzyme-linked polyclonal antibody specific for TNF-α can be added to the wells. Following a wash to remove any unbound antibody-enzyme reagent, a substrate solution can be added to the wells and color develops in proportion to the amount of TNF-α bound in the initial step using a microplate reader for detection at 450 nm. The color development can be stopped and the intensity of the color can be measured. Subconfluent normal human adult keratinocytes (Cascade Biologics) cultivated in EpiLife standard growth medium (Cascade Biologics) at 37° C. in 5% $CO_2$, can be treated with phorbol 12-myristate 13-acetate (PMA, 10 ng/ml, Sigma Chemical, #P1585-1MG) and any one of the active ingredients, combination of ingredients, or compositions having said combinations disclosed in the specification for 6 hours. PMA has been shown to cause a dramatic increase in TNF-α secretion which peaks at 6 hours after treatment. Following incubation, cell culture medium can be collected and the amount of TNF-α secretion quantified using a sandwich enzyme linked immuno-sorbant assay (ELISA) from R&D Systems (#DTA00C).

Antioxidant (AO) Assay:

An in vitro bioassay that measures the total anti-oxidant capacity of any one of the ingredients, combination of ingredients, or compositions having said combinations disclosed in the specification. The assay relies on the ability of antioxidants in the sample to inhibit the oxidation of ABTS® (2,2'-azino-di-[3-ethylbenzthiazoline sulphonate]) to ABTS®•+ by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the antioxidants in the sample to prevent ABTS oxidation is compared with that of Trolox, a water-soluble tocopherol analogue, and is quantified as molar Trolox equivalents. Anti-Oxidant capacity kit #709001 from Cayman Chemical (Ann Arbor, Mich. USA) can be used as an in vitro bioassay to measure the total anti-oxidant capacity of each of any one of the active ingredients, combination of ingredients, or compositions having said combinations disclosed in the specification. The protocol can be followed according to manufacturer recommendations. The assay relied on antioxidants in the sample to inhibit the oxidation of ABTS® (2,2'-azino-di-[3-ethylbenzthiazoline sulphonate]) to ABTS®•+ by metmyoglobin. The capacity of the antioxidants in the sample to prevent ABTS oxidation can be compared with that Trolox, a water-soluble tocopherol analogue, and was quantified as a molar Trolox equivalent.

ORAC Assay:

Oxygen Radical Absorption (or Absorbance) Capacity (ORAC) of any one of the active ingredients, combination of ingredients, or compositions having said combinations disclosed in the specification can also be assayed by measuring the antioxidant activity of such ingredients or compositions. This assay can quantify the degree and length of time it takes to inhibit the action of an oxidizing agent such as oxygen radicals that are known to cause damage cells (e.g., skin cells). The ORAC value of any one of the active ingredients, combination of ingredients, or compositions having said combinations disclosed in the specification can be determined by methods known to those of ordinary skill in the art (see U.S. Publication Nos. 2004/0109905 and 2005/0163880; Cao et al. (1993)), all of which are incorporated by reference). In summary, the assay described in Cao et al. (1993) measures the ability of antioxidant compounds in test materials to inhibit the decline of B-phycoerythrm (B-PE) fluorescence that is induced by a peroxyl radical generator, AAPH.

Mushroom Tyrosinase Activity Assay:

In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. Purified mushroom tyrosinase (Sigma) can be incubated with its substrate L-Dopa (Fisher) in the presence or absence of each of the active ingredients, any one of the combination of ingredients, or compositions having said combinations disclosed in the specification. Pigment formation can be evaluated by colorimetric plate reading at 490 nm. The percent inhibition of mushroom tyrosinase activity can be calculated compared to non-treated controls to determine the ability of test ingredients or combinations thereof to inhibit the activity of purified enzyme. Test extract inhibition was compared with that of kojic acid (Sigma).

Matrix Metalloproteinase Enzyme Activity (MMP3; MMP9) Assay:

An in vitro matrix metalloprotease (MMP) inhibition assay. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG-[2-mercapto-4-methylpentanoyl]-LG-$OC_2H_5$)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm (c=13,600 M-1 cm-1 at pH 6.0 and above 7). The active ingredients, any one of the combination of ingredients, or compositions having said combinations disclosed in the specification can be assayed.

Cyclooxygenase (COX) Assay:

An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors. The Colormetric COX (ovine) Inhibitor screening assay (#760111, Cayman Chemical) can be used to analyze the effects of each of the active ingredients, any one of the combination of ingredients, or compositions having said combinations disclosed in the specification on the activity of purified cyclooxygnase enzyme (COX-1 or COX-2). According to manufacturer instructions, purified enzyme, heme and test extracts can be mixed in assay buffer and incubated with shaking for 15 min at room temperature. Following incubation, arachidonic acid and colorimetric substrate can be added to initiate the reaction. Color progression can be evaluated by colorimetric plate reading at 590 nm. The percent inhibition of COX-1 or COX-2 activity can be calculated compared to non-treated controls to determine the ability of test extracts to inhibit the activity of purified enzyme.

Lipoxygenase (LO) Assay:

An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives, that are subsequently converted to leukotirenes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid. The Colorimetric LO Inhibitor screening kit (#760700, Cayman Chemical) can be used to determine the ability of each of the active ingredients, any one of the combination of ingredients, or compositions having said combinations disclosed in the specification to inhibit enzyme activity. Purified 15-lipoxygenase and test ingredients can be mixed in assay buffer and incubated with shaking for 10 min at room temperature. Following incubation, arachidonic acid can be added to initiate the reaction and mixtures incubated for an additional 10 min at room temperature. Colorimetric substrate can be added to terminate catalysis and color progression was evaluated by fluorescence plate reading at 490 nm. The percent inhibition of lipoxyganse activity can be calculated compared to non-treated controls to determine the ability of each of the active ingredients, any one of the combination of ingredients, or compositions having said combinations disclosed in the specification to inhibit the activity of purified enzyme.

Elastase Assay:

EnzChek® Elastase Assay (Kit #E-12056) from Molecular Probes (Eugene, Oreg. USA) can be used as an in vitro enzyme inhibition assay for measuring inhibition of elastase activity for each of the active ingredients, any one of the combination of ingredients, or compositions having said combinations disclosed in the specification. The EnzChek kit contains soluble bovine neck ligament elastin that can be labeled with dye such that the conjugate's fluorescence can be quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at ~505 nm and fluorescence emission maxima at ~515 nm. The peptide, chloromethyl ketone, can be used as a selective, collective inhibitor of elastase when utilizing the EnzChek Elastase Assay Kit for screening for elastase inhibitors.

Oil Control Assay:

An assay to measure reduction of sebum secretion from sebaceous glands and/or reduction of sebum production from sebaceous glands can be assayed by using standard techniques known to those having ordinary skill in the art. In one instance, the forehead can be used. Each of the active ingredients, any one of the combination of ingredients, or compositions having said combinations disclosed in the specification can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin. This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion.

Erythema Assay:

An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with the active ingredients, any one of the combination of ingredients, or compositions having said combinations disclosed in the specification. Repeat measurements can be taken at regular intervals to determine the formula's ability to reduce redness and irritation.

Skin Moisture/Hydration Assay:

Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance. Each of the active ingredients, any one of the combination of ingredients, or compositions having said combinations disclosed in the specification can be assayed according to this process.

Skin Clarity and Reduction in Freckles and Age Spots Assay:

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether each of the active ingredients, any one of the combination of ingredients, or compositions having said combinations disclosed in the specification is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay:

Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay:

Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay:

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay with Methods Disclosed in Packman et al. (1978):

Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer:

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer:

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas:

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and are of the replicas covered by wrinkles or fine lines was determined.

Surface Contour of the Skin Assay with a Profilometer/Stylus Method:

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $I_m$=the traverse (scan) length; and y=the absolute value of the location of the profile relative to the mean profile height (x-axis).

MELANODERM™ Assay:

In other non-limiting aspects, the efficacy of each of the active ingredients, any one of the combination of ingredients, or compositions having said combinations disclosed in the specification compositions can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing each of the active ingredients, any one of the combination of ingredients, or compositions having said combinations disclosed in the specification or with the base alone as a control. Alternatively, an untreated sample of the skin analog can be used as a control.

All of the compositions and/or methods disclosed and claimed herein can be made and executed without undue experimentation in light of the present disclosure. While the compositions and methods disclosed herein have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method of exfoliating skin and counteracting skin irritation caused by an exfoliant, the method comprising topically applying an effective amount of a skin exfoliation composition to skin in need thereof, wherein the composition comprises:
   an effective amount of an alpha hydroxy acid to exfoliate the skin; and
   an effective amount of a combination of:
      4-tert-butylcyclohexanol;
      an aqueous extract of plankton comprising an exopolysacchride synthesized by *Vibrio alginolyticus;*
      an aqueous extract of *Phragmites communis;*
      an aqueous extract of *Poria cocos;* and
      an aqueous extract of *Cucurbita pepo* (pumpkin) seed, to counteract skin irritation caused by the alpha hydroxy acid.

2. The method of claim 1, wherein the skin is facial skin.

3. The method of claim 2, wherein the composition remains on the facial skin for up to 15 minutes and is then removed from the skin.

4. The method of claim 1, wherein the composition is applied to a fine line or wrinkle.

5. The method of claim 1, wherein the composition is applied to skin having an uneven skin tone.

6. The method of claim 5, wherein the uneven skin tone comprises hyperpigmented or melasmic skin.

7. The method of claim 5, wherein the uneven skin tone comprises hyperpigmented skin, and wherein the hyperpigmented skin is an age spot, a liver spot or a dark spot on the skin.

8. The method of claim 1, wherein the composition is an emulsion.

9. The method of claim 8, wherein the emulsion is an oil-in-water emulsion.

10. The method of claim 1, wherein the composition further comprises:
    triethanolamine;
    glycerin;
    butylene glycol;
    sea water;
    cetearyl alcohol;
    arachidyl alcohol;
    sorbitan isostearate;
    dicaprylyl carbonate;
    biosaccharide gum-1; and
    behenyl alcohol.

11. The method of claim 1, wherein the composition comprises:
    2 wt. % to 20 wt. % of the alpha hydroxy acid;
    0.0001 wt. % to 5 wt. % of 4-tert-butylcyclohexanol;
    0.0001 wt. % to 5 wt. % of the aqueous extract of plankton comprising an exopolysacchride synthesized by *Vibrio alginolyticus;*
    0.0001 wt. % to 5 wt. % of the aqueous extract of *Phragmites communis;*
    0.0001 wt. % to 5 wt. % of the aqueous extract of *Poria cocos;* and
    0.0001 wt. % to 5 wt. % of the aqueous extract of *Cucurbita pepo* (pumpkin) seed.

12. The method of claim 1, wherein:
    the alpha hydroxy acid exfoliates the skin;
    4-tert-butylcyclohexanol reduces irritation of the skin;
    the aqueous extract of plankton comprising an exopolysacchride synthesized by *Vibrio alginolyticus* reduces inflammation in the skin;
    the aqueous extract of *Phragmites communis* reduces inflammation in the skin;
    the aqueous extract of *Poria cocos* reduces inflammation in the skin; and
    the aqueous extract of *Cucurbita pepo* (pumpkin) seed increases collagen production in the skin and inhibits MMP3 activity in the skin.

13. The method of claim 1, wherein the composition is formulated as a facial peel.

14. The method of claim 1, wherein the alpha hydroxy acid is glycolic acid.

* * * * *